US011740220B2

(12) United States Patent
Sans-Jofre et al.

(10) Patent No.: US 11,740,220 B2
(45) Date of Patent: Aug. 29, 2023

(54) DEVICE AND METHOD FOR CONTINUOUS ANALYSIS OF THE CONCENTRATION OF DISSOLVED INORGANIC CARBON (DIC) AND OF THE ISOTOPIC CARBON AND OXYGEN COMPOSITIONS THEREOF

(71) Applicants: Centre National de la Recherche Scientifique, Paris (FR); Université de Bretagne Occidentale—UBO, Brest (FR)

(72) Inventors: Pierre Sans-Jofre, Charenton-le-Pont (FR); Stefan Lalonde, Brest (FR); Céline Liorzou, Brest (FR)

(73) Assignees: CENTRE NATIONAL DE LA RECHERCHE SCIENTIFIQUE, Paris (FR); UNIVERSITÉ DE BRETAGNE OCCIDENTALE—UBO, Brest (FR)

( * ) Notice: Subject to any disclaimer, the term of this patent is extended or adjusted under 35 U.S.C. 154(b) by 867 days.

(21) Appl. No.: 16/629,362

(22) PCT Filed: Jul. 9, 2018

(86) PCT No.: PCT/FR2018/051715
§ 371 (c)(1),
(2) Date: Jan. 8, 2020

(87) PCT Pub. No.: WO2019/012212
PCT Pub. Date: Jan. 17, 2019

(65) Prior Publication Data
US 2020/0150105 A1    May 14, 2020

(30) Foreign Application Priority Data
Jul. 10, 2017    (FR) ..................... 1756500

(51) Int. Cl.
*G01N 33/18* (2006.01)
*B01D 19/00* (2006.01)
*G01N 35/10* (2006.01)

(52) U.S. Cl.
CPC ..... *G01N 33/1846* (2013.01); *B01D 19/0005* (2013.01); *B01D 19/0036* (2013.01); *G01N 35/1097* (2013.01)

(58) Field of Classification Search
None
See application file for complete search history.

(56) References Cited

U.S. PATENT DOCUMENTS 4,277,438 A    7/1981    Ejzak
5,459,075 A    10/1995    Fabinski
(Continued)

FOREIGN PATENT DOCUMENTS

CN    201555755 U    8/2010
CN    105806689 A    7/2016
WO    2015179871 A1    11/2015

OTHER PUBLICATIONS

International Search Report for corresponding application PCT/FR2018/051715 filed Jul. 9, 2018; dated Oct. 4, 2018.
(Continued)

*Primary Examiner* — Christopher P Jones
*Assistant Examiner* — Phillip Y Shao
(74) *Attorney, Agent, or Firm* — Cantor Colburn LLP (57) ABSTRACT

The present invention relates to a novel analysis device and method for obtaining the concentration of dissolved inorganic carbon (DIC) and isotopic carbon and oxygen concentration thereof, continuously from a liquid sample.

15 Claims, 12 Drawing Sheets

(56) References Cited

U.S. PATENT DOCUMENTS 8,114,676 B2    2/2012  Conway
2006/0210961 A1    9/2006  Magnaldo
2010/0212406 A1    8/2010  Browne

OTHER PUBLICATIONS

Written Opinion for corresponding application PCT/FR2018/051715 filed Jul. 9, 2018; dated Oct. 4, 2018.
Assayag et al., Rapid Communications in Mass Spectrometry, 20(15) : 2243-2251, 2006.
Bass et al., Rapid Communications in Mass Spectrometry, 26(6) : 639-644, 2012.
Smajgl et al. 2017, "Using Isotope Ratio Infrared Spectrometer to determine 13C and 18O of carbonate samples", 19th EGU General Assembly, EGU2017, proceedings from the conference held Apr. 23-28, 2017 in Vienna, Austria., p. 9793.

| Sample | Classic method | | | Continuous method | | |
|---|---|---|---|---|---|---|
| | Number of measurements | δ13C (VPDB‰) | ± | Number of measurements | δ13C (VPDB‰) | ± |
| NaHCO3 | 3 | -5.78 | 0.14 | 6 | -6.09 | 0.21 |
| Na2CO3 | 4 | -6.67 | 0.07 | 32 | -7.10 | 0.32 |
| VOLVIC | 2 | -9.88 | 0.10 | 2 | -11.25 | 0.04 |
| HEPAR | 2 | -13.32 | 0.10 | 2 | -14.51 | 0.06 |
| CRISTALLINE | 3 | -12.81 | 0.03 | 2 | -14.08 | 0.16 |
| EVIAN | 2 | -12.11 | 0.07 | 2 | -13.27 | 0.11 |
| PLANCOET | 1 | -15.10 | | 4 | -15.75 | 0.52 |
| MONT BLANC | 3 | -9.88 | 0.16 | 2 | -10.72 | 0.15 |

| Sample | Classic method δ18O (VPDB-CO2‰) | | | Continuous method δ18O (VPDB-CO2‰) | |
|---|---|---|---|---|---|
| | Number of measurements | δ18O (VPDB-CO2‰) | ± | δ18O (VPDB-CO2‰) | ± |
| NaHCO3 | 3 | -7.74 | 0.11 | -7.03 | 0.15 |
| Na2CO3 | 4 | -7.71 | 0.23 | -8.91 | 0.33 |
| VOLVIC | 2 | -8.89 | 0.02 | -8.95 | 0.30 |
| HEPAR | 2 | -8.31 | 0.23 | -7.80 | 0.05 |
| CRISTALLINE | 3 | -5.68 | 0.07 | -5.88 | 0.28 |
| EVIAN | 2 | -10.57 | 0.06 | -10.64 | 0.00 |
| PLANCOET | 1 | -6.57 | | -7.02 | 0.31 |
| Eau de mer | 2 | -0.59 | 0.50 | -0.77 | 0.04 |
| MONT BLANC | 3 | -14.09 | 0.50 | -13.53 | 0.03 |

|  | continuous method | Reading on the bottle |
|---|---|---|
| Volvic | 220 | 74 |
| Evian | 834 | 360 |
| Cristalline ELEONORE | 597 | 236 |
| Contrex | 855 | 372 |
| Vittel | 859 | 384 |
| Mont Blanc | 208 | 65 |
| Plancoët | 325 | 121 |

FIGURE 7

DEVICE AND METHOD FOR CONTINUOUS ANALYSIS OF THE CONCENTRATION OF DISSOLVED INORGANIC CARBON (DIC) AND OF THE ISOTOPIC CARBON AND OXYGEN COMPOSITIONS THEREOF

TECHNICAL FIELD OF THE INVENTION

The present invention relates to a novel analysis device and method for obtaining the concentration of dissolved inorganic carbon (DIC) and/or the isotopic carbon and oxygen concentration thereof, continuously.

The present invention finds applications in various fields such as, for example: the monitoring of pollutant emissions in rivers; the monitoring of water quality (water table, swimming pool, wastewater treatment plant, pharmaceutical industry, production of electronic materials, etc.); the detection of wine and champagne fraud by isotopic analysis, volcanic observation; biology, detection of plankton blooms and eutrophication of lakes; continuous monitoring of ocean acidification caused by global warming; monitoring and contamination of water tables. The present invention also opens up a new research discipline field, whether in biology or geology, which is the analysis of rapid isotopic variations and rapid variations in DIC concentration over periods of more or less lengthy duration.

In the description below, the references between square brackets ([ ]) refer to the list of references presented at the end of the text.

PRIOR ART

The most common method for analyzing the DIC concentration is the titration of a liquid sample with a basic solution of known concentration, either $Na_2CO_3$, or NaOH, at the point of equivalence of the phenolphthalein indicator (pH 8.3) (e.g., Method 4500-$CO_2$ dans Rice E W, Bridgewater L, Association APH, Association AWW, Federation WE «Standard Methods for the Examination of Water and Wastewater», Am. Public Health Assn., 2012) [1]. Other systems exist, which convert the DIC to $CO_2$ via the acidification of a liquid sample in a reaction chamber, followed by the passing of the $CO_2$ produced to a detection system. These detection systems are principally based on infrared laser absorption techniques (e.g., AS-C3, Apollo SciTech, LLC), but also on other detection techniques, such as colorimetric changes (e.g., CM140 Total Inorganic Carbon Analyzer, UIC, Inc.). However, all of these methods remain isolated DIC analysis methods.

The method used up until now for analyzing the isotopic oxygen and carbon composition of DIC is based on isolated mixing of the aqueous sample with orthophosphoric acid in a tube which has been hermetically sealed and from which the initial $CO_2$ has been removed (Assayag et al., 2006) [2]. This mixing can also be carried out in a reaction chamber (Bass et al., 2012) [3]. This step is followed by an equilibration time ranging from about ten minutes and possibly reaching several hours (Bass et al., 2012; Assayag et al., 2006). The $CO_2$ produced is then sent to a detection system comprising principally gas mass spectrometers (IRMS, e.g., Delta V, Thermo Fisher) and more rarely infrared spectrometers (e.g., Delta Ray, Picarro). These two methods are isolated analysis techniques which require the taking of samples which are stored and then subsequently treated in a laboratory. The techniques used are time consuming and expensive, and do not make it possible to perform analyses continuously in the laboratory or even in the field.

Some systems for continuous measurement of DIC concentration are described in the art (patent application US 2010/0212406) [4].

However, the speed of measurement in these techniques is generally insufficient (e.g., greater than tens of seconds), and these techniques are not compatible with an objective obtaining of isotope ratios.

There is thus a need for a method for continuous analysis of the concentration and of the isotopic carbon and oxygen composition of dissolved inorganic carbon (DIC).

DESCRIPTION OF THE INVENTION

The inventors have developed a system which allows the continuous analysis of the concentration and the continuous analysis of the isotopic carbon and oxygen compositions of Dissolved Inorganic Carbon (DIC) on the scale of one second, via the permanent chemical production of $CO_2$ (gas) from the DIC, then a gas-liquid separation leading the continuous stream of $CO_2$ produced to a detector of infrared laser spectrometer type. A peristaltic pump controls the mixing of the two liquids (sample and anhydric acid) which causes a production of $CO_2$. This $CO_2$ is separated from the residual liquids and conveyed, by virtue of a vector gas, to an analyzer. This system thus allows the continuous monitoring of the concentrations and isotopic carbon and oxygen compositions of DIC. The tests have shown that the gases recovered make it possible to obtain the DIC concentration, and also the precise isotopic carbon and oxygen compositions thereof, continuously, without stagnation in a momentarily closed chamber.

The inventors have thus carried out, for the first time, a production of $CO_2$ which is constant over time, by virtue of rapid degassing of the $CO_2$ from a liquid reservoir, for a given concentration of $CO_2$. This has made is possible to establish a linear relationship between the $CO_2$ concentration of the stream leaving the gas-liquid separator and the DIC concentration of the sample analyzed. The performing of the degassing and the rapid and efficient gas-liquid separation on the scale of one second makes it possible to control and to dispense with the problems of isotopic equilibration, in particular between the oxygen of the $CO_2$ produced and that of the liquid water. Thus, this technique has also made it possible to directly obtain, on the scale of one second, the isotopic carbon and oxygen composition of the DIC in the sample from the $CO_2$ produced.

In order to achieve such a separation, the inventors have turned to existing systems which allow the production and separation of gas from a mixture of reagent and effluent to be analyzed: hydride generators. The introduction system, sold by a handful of manufacturers (e.g., Teledyne-CETAC, ESI Inc., etc.), serves to mix a highly reducing reagent (e.g., $NaBH_4$) with acid (HCl) and an effluent with the aim of generating gaseous hydrides of metals and metalloids (e.g., Ge, Se, Sb, Hg). These hydrides are then sent to an analyzer of ICP-AES or ICP-MS type by direct coupling via the use of an inert vector gas (argon). In the context of the present invention, the inventors have used the high capacity of the hydride generators to perform the physical mixing, the chemical reaction, the gas separation and the gas sampling, for studying the gases naturally dissolved in fluids, such as $CO_2$, but by diverting them from their initial operation. To do this, they have had to modify the branching of a hydride generator (hybrideICP, model HG-MP2-4-A, ESI Inc.) to produce a continuous $CO_2$ fluid with a concentration proportional to that of the DIC and bearing its (carbon and oxygen) isotopic signature in the following way:

replacement of the conventional acids with concentrated orthophosphoric acid (85-102%). This has made it possible to decrease the interaction with the water naturally contained in the other conventional mineral acids (HCl, HNO$_3$, H$_2$SO$_4$, HF). In addition, this new assembly has proven to be also efficient in the production of CO$_2$ with other acids.

Contrary to the conventional hydride-generating methods which require a reducing reagent to reduce the analyte in question to its hydride form, in the context of the present invention, no other reagent is necessary to generate gas (i.e., CO$_2$) from the effluent. To do this, the reducing-agent inlet of the hybrideICP was blocked, thus allowing the hydride generator to be fed only with two reagents and no longer three: the acidifying reagent and the sample to be analyzed.

Instead of an inert gas vector suitable for the plasma-source spectrometric analysis (argon), gases compatible with the spectrometers dedicated to the carbon and oxygen isotope analysis were selected. For the isotope-ratio spectrometers (IRMS), helium is the vector gas, and for the spectrometers of cavity ring-down type (ORDS; model G2131-i, Picarro Inc.) or isotope ratio infrared spectrometers (IRIS), such as the Delta ray model, Thermo Fisher Inc., the vector gas is CO$_2$-free synthetic air. These gas vector choices protect the ionization source (in the case of IRMSs) or optimize the optical conditions internal to the instruments (in the CRDS and IRIS types). The present invention also applies to IRMS and CRDS/IRIS instruments in terms of its capacity to provide a continuous stream of CO$_2$ bearing the composition of the DIC in the effluent entering the gas-liquid separator.

The mixing conditions (length of a loop for reaction between the acid and the effluent, proportion of acid and of the effluent in the mixture) and also the production of CO$_2$ (pump speed, diameter of the pipes bringing the acid and the effluent into the mixture) are optimized for maximum production of CO$_2$.

An excess gas outlet of open-slit type can be added between the gas-liquid separator and the analysis system for adjusting and optimizing the pressure of the gases entering the analysis system.

The effluent is suctioned and mixed and undergoes a gas-liquid separation. The CO$_2$ given off is brought as a continuous stream to the analysis system, over extremely short timescales (generally on the scale of one second to one minute).

Independently of the time taken for the effluent to enter the gas-liquid separator system and for the CO$_2$ produced to reach the analysis system, the present invention allows the analysis of the change in the concentrations and isotopic compositions of the DIC on a scale which is limited only by the residence time of the gases in the gas-liquid separator and the mixing processes during the transport between the gas-liquid separator and the analyzer. According to a first prototype (gas-liquid separator volume of approximately 10 cm$^3$), the scale has been estimated to be about 1 to 6 seconds depending mainly on the volume of the separation chamber. This timescale can further be decreased below one second by reducing the volume of the gas-liquid separator, by increasing the continuous stream of the vector gas and by shortening the distance of the connections between the gas-liquid separator and the analyzer.

Thus, the assembly of the present invention has made it possible to directly obtain, on the scale of one second, the concentration and the carbon and oxygen isotopic compositions of DIC in liquid effluents.

Figure 1:
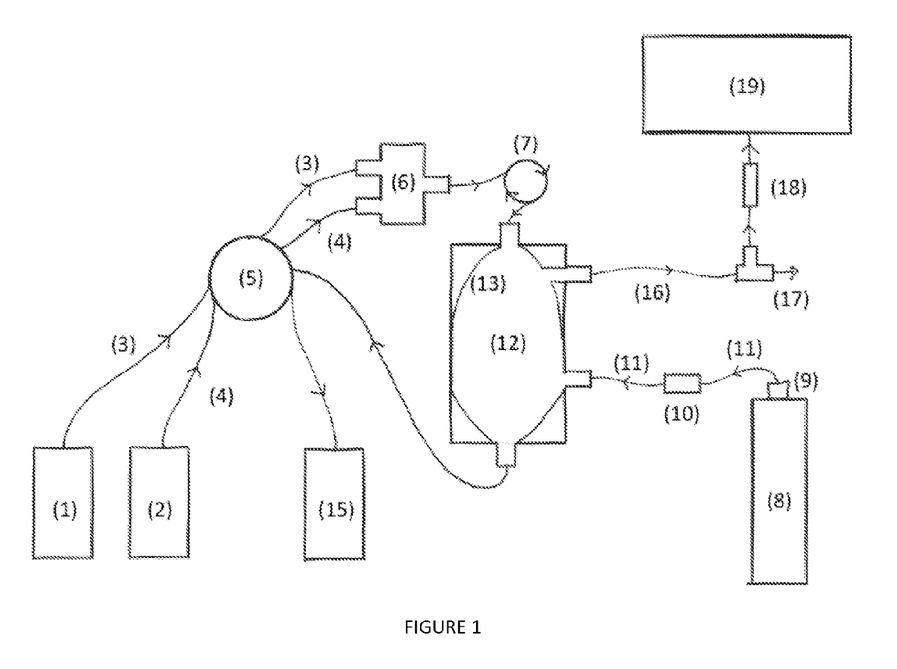
FIG. 1 represents a simplified diagram of an embodiment of an exemplary version of a device of the present invention.
Figure 2:
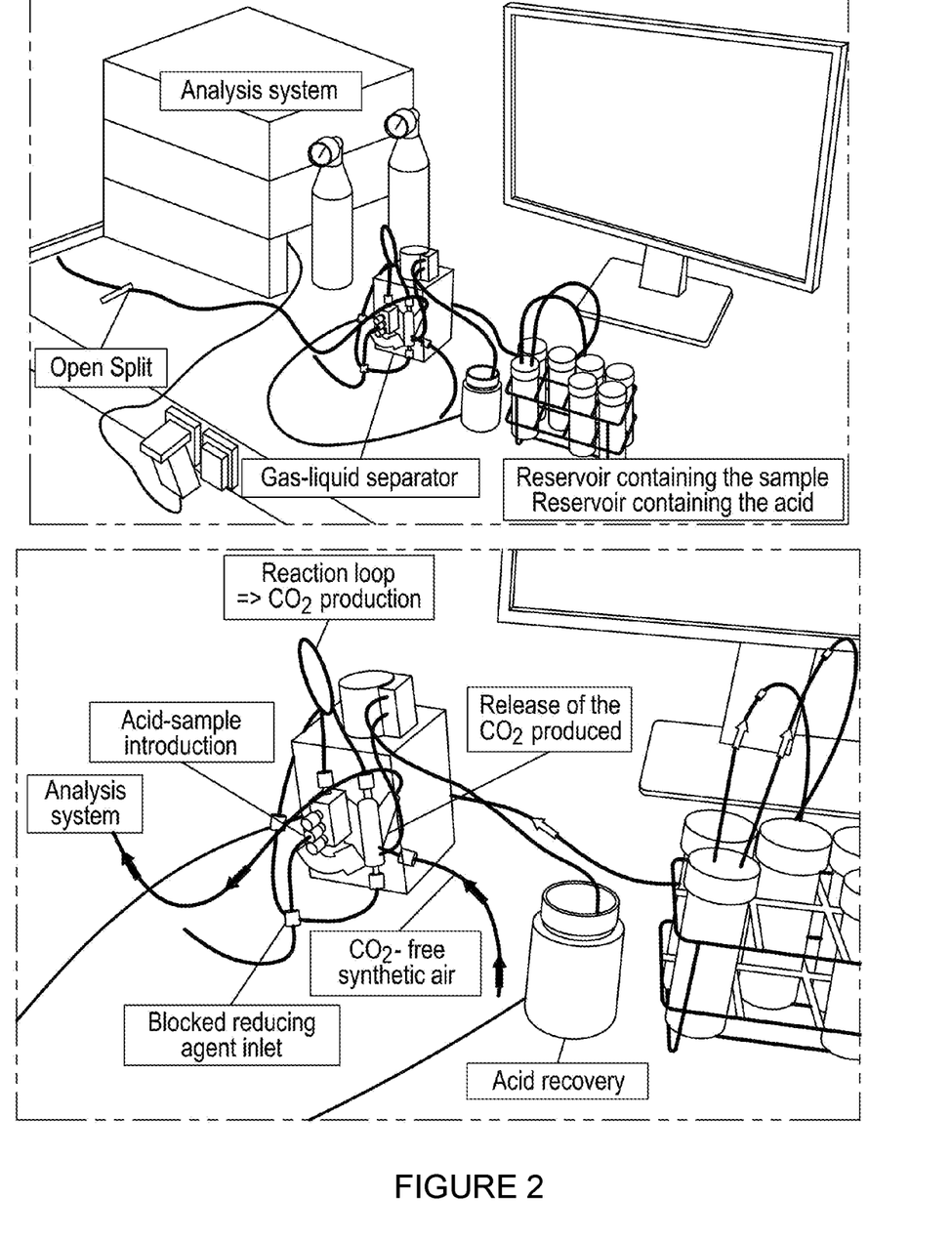
FIG. 2 represents an exemplary prototype of a device of the present invention.

The present invention thus relates to a method and a device for analyzing the concentration and/or the carbon and oxygen isotopic compositions of dissolved inorganic carbon (DIC) in a liquid sample. Said device comprises or consists of an assembly of tubes connected to a peristaltic pump (5) which makes it possible to inject and mix two fluids with a precise flow. The mixture consists of a liquid sample and an acidifying reagent which serves to force the equilibrium in the thermodynamic reactions of the DIC system toward CO$_2$ gas. This mixture is released into a glass enclosure, which is a gas-liquid separation chamber (12), which serves to recover the gas produced in a continuous flow of vector gas (16), and to send the gas mixture containing the CO$_2$ derived from the DIC into an analyzer of infrared laser spectrometer type (19). These tubes are each connected to a reservoir. The reservoir (1) contains the liquid sample to be analyzed. The reservoir (2) contains an anhydric acid (e.g., H$_3$PO$_4$>85%). These two fluids are conveyed to the peristaltic pump (5) with constant flows, F1 (3) and F2 (4), respectively. These fluids are dynamically mixed in a mixing chamber (6) then carried in a reaction loop (7) of which the length can vary depending on the type of sample to be analyzed. In this reaction loop (7), an acid-based reaction makes it possible to convert the DIC into CO$_2$ gas, in the presence of an excess of acid. This mixture of gas and liquid is conveyed into a separation chamber (12) which makes it possible to cover the CO$_2$ gas produced. This chamber (12) is connected at the bottom to a vector-gas cylinder (8) containing CO$_2$-free synthetic air. This gas generally consists of 20% dioxygen, and 79% dinitrogen and 1% argon. This mixture can vary as a function of the detection system used. The flow (11) is controlled by a pressure regulator (9) and a control unit (10) which makes it possible to modify, by computer, this flow (11), in order to optimize the amount of CO$_2$ arriving at the detection system (19). The vector gas (without CO$_2$) is sent into the separation chamber (12) and captures the CO$_2$ produced during the reaction in the reaction loop (7) and released in the separation chamber (12). This chamber (12) can have a wall with an extended and treated surface (e.g., frosted glass) so as to optimize the degassing (13). On one side, the residual fluid (containing the acid and the degassed sample) is pumped and recovered in a waste reservoir (15), and on the other, the vector gas (16) makes it possible to transport the CO$_2$ degassed from the sample. This gas (16) can optionally pass via an open-split (17) for an adjustment of the flows as a function of the requirements of the detection system, before passing through a water- and particle-trap (18) and an analyzer of infrared laser spectrometer type (19).

A subject of the present invention is thus a device for continuous analysis of the concentration of dissolved inorganic carbon (DIC) and/or of the isotopic carbon and oxygen compositions thereof in a liquid sample, said device comprising or consisting of:
  an assembly of tubes, each connected to a reservoir (1),(2), each containing a fluid, and connected to a pump (5) positioned downstream of said tubes;
  a mixing chamber (6) positioned downstream of the pump (5) and wherein the fluids conveyed to the pump (5) are dynamically mixed;

a reaction loop (7) positioned downstream of the reaction chamber (6), said reaction loop (7) making it possible to convert the DIC into $CO_2$ gas according to an acid-base reaction;

a separation chamber (12) positioned downstream of the reaction loop (7), said separation chamber (12) also being connected to a vector-gas cylinder (8) containing $CO_2$-free vector gas;

a pressure regulator (9) and a control unit (10) positioned between the vector-gas cylinder (8) and the separation chamber (12) and which control the flow (11) of vector gas sent from the vector-gas cylinder (8) into the separation chamber (12) for capturing the $CO_2$ produced in the reaction loop (7);

a waste reservoir (15) positioned downstream of the separation chamber (12) for recovering, via the pump (5), the degassed residual fluids;

a water- and particle-trap (18) positioned downstream of the separation chamber;

optionally, an excess gas outlet of open-split type (17) positioned between the separation chamber (12) and the water- and particle-trap (18) in order to adjust the flows;

a detection system (19) positioned downstream of the water- and particle-trap (18).

According to one particular embodiment of the device of the present invention, the reaction chamber (12) comprises a wall with an extended and treated surface in order to optimize the degassing (13). For example, the wall of the separation chamber (12) is made of frosted glass.

According to one particular embodiment of the device of the present invention, the reservoir (1) contains the liquid sample to be analyzed, and the reservoir (2) contains an acidifying reagent, preferably an anhydric acid, most preferentially an orthophosphoric acid.

According to one particular embodiment of the device of the present invention, the detection system (19) is an analyzer of isotope-ratio infrared spectrometer (IRIS) type.

According to one particular embodiment of the device of the present invention, the vector gas is chosen from helium and $CO_2$-free synthetic air (i.e. a mixture comprising 20% oxygen, 79% nitrogen and 1% argon).

A subject of the present invention is also a method for continuous analysis of the concentration of dissolved inorganic carbon (DIC) and/or of the isotopic carbon and oxygen compositions thereof in a liquid sample, said method comprising or consisting of:

a) conveying the liquid sample to be analyzed and an acidifying reagent to a pump (5) with constant flows F1 (3) and F2 (4), respectively;

b) injecting and mixing the two fluids in a mixing chamber (6);

c) conveying the mixture of fluids obtained in step b) to a reaction loop (7) wherein an acid-base reaction makes it possible to totally or partially convert the DIC into $CO_2$ gas;

d) conveying the mixture of gas and liquid obtained in step c) into a separation chamber (12);

e) injecting a flow (11) of vector gas devoid of $CO_2$ into the separation chamber (12) in order to capture the $CO_2$ gas produced during step c) and released (13) in the separation chamber (12);

f) conveying the flow (16) of vector gas containing the $CO_2$ degassed from the sample, obtained in step e), through a water- and particle-trap (18), optionally after a passage through an open-split (17) for a flow adjustment;

g) conveying the residual fluid composed of the acidifying reagent and of the degassed sample into a waste reservoir (15);

h) conveying the flow (16) of vector gas containing the $CO_2$ gas derived from the DIC into a detection system (19);

i) determining the concentration of dissolved inorganic carbon (DIC) and/or the isotopic carbon and oxygen compositions by means of said detection system (19).

According to one particular embodiment of the method of the present invention, step a) is carried out under constant flows F1 (3) of sample and F2 (4) of acidifying reagent of the order of approximately 750 µl/min and of approximately 190 µl/min, respectively. This gives a sample/acidifying reagent ratio of approximately 4.

According to one particular embodiment of the method of the present invention, step c) is carried out in the presence of an excess of acid for optimal conversion of the DIC into $CO_2$ gas.

According to one particular embodiment of the method of the present invention, step e) is carried out with a reaction loop of which the length ranges, for example from 0.5 to 4.5 ml, as a function of the sample to be analyzed.

According to one particular embodiment of the method of the present invention, step e) uses a vector gas chosen from helium and $CO_2$-free synthetic air (i.e. a mixture comprising 20% oxygen, 79% nitrogen and 1% argon).

According to one particular embodiment of the method of the present invention, the flow (11) is controlled by a pressure regulator (9) and a control unit (10) in order to optimize the amount of $CO_2$ gas arriving at the detection system (19).

According to one particular embodiment of the method of the present invention, step a) is carried out with an acidifying reagent which is an anhydric acid, preferably an orthophosphoric acid.

According to one particular embodiment of the method of the present invention, step i) is carried out by means of an analyzer of isotope-ratio infrared spectrometer (IRIS) type.

BRIEF DESCRIPTION OF THE FIGURES

FIG. 4 represents the effects of the concentration on the carbon (D13C) and oxygen (D18O) isotopic values of various liquid samples: (A) in $Na_2CO_3$, (B) in $NaHCO_3$.

FIG. 5 represents the effects of the pump speed on the $CO_2$ concentration of the DIC (A) in Plancoët mineral water, $Na_2CO_3$ and $NaHCO_3$, and the isotopic carbon values of the DIC (B) in Plancoët mineral water, $Na_2CO_3$ and $NaHCO_3$ and isotopic oxygen values of the DIC (C) in Plancoët mineral water, $Na_2CO_3$ and $NaHCO_3$.

FIG. 6 represents the effects of the length of the reaction or mixing loop on the $CO_2$ concentrations of the DIC (A) in Plancoët mineral water, $Na_2CO_3$ and $NaHCO_3$, and the isotopic carbon values of the DIC (B) in Plancoët mineral water, $Na_2CO_3$ and $NaHCO_3$, and isotopic oxygen values of the DIC (C) in Plancoët mineral water, $Na_2CO_3$ and $NaHCO_3$.

EXAMPLES

Example 1: Comparison of the Isotopic Carbon and Oxygen Compositions of the Dic of Liquid Samples Obtained by a Conventional Analysis Method with Equilibration and by the Analysis Method of the Invention For this experiment, 7 mineral waters and a seawater were measured for $\delta^{13}C$ and $\delta^{18}O$ in order to compare the measurements obtained with the hydride generator used according to the present invention and with the conventional equilibration method (Smajgl et al. 2017 19th EGU General Assembly, EGU2017, proceedings from the conference held Apr. 23-28, 2017 in Vienna, Austria., p. 9793) [6]. The 2 types of measurements were carried out on a Delta Ray instrument. The straight lines of correlation between the methods have correlation coefficients of 0.99.

Figure 3:
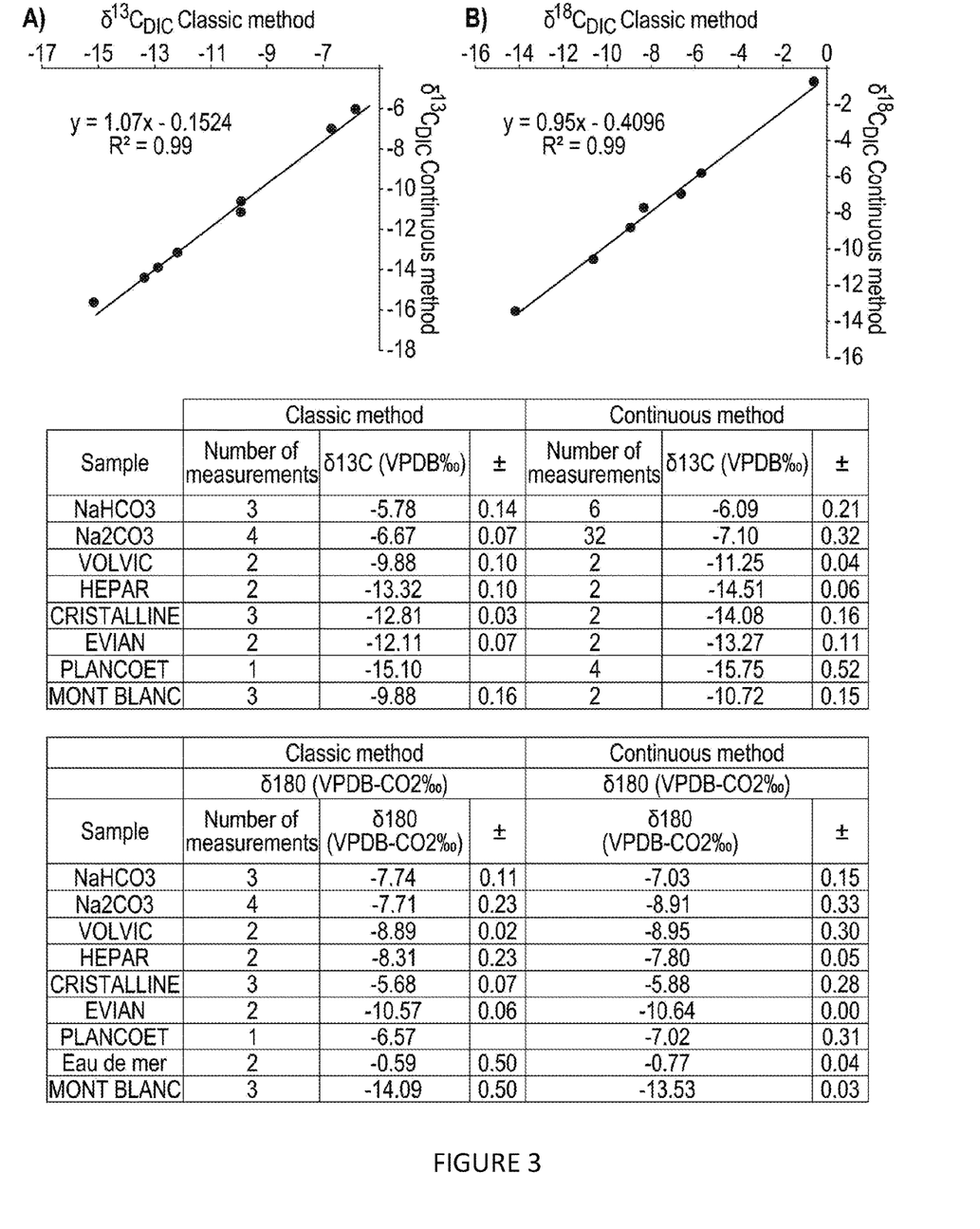
FIG. 3 represents the results of measurement of the carbon (D13C) and oxygen (D18O) isotope ratios of the DIC of various liquid samples obtained by a conventional analysis method with equilibration and the analysis method according to the present invention. (A) graph of comparison of the results obtained for the two methods (conventional method and continuous method) for the carbon isotopes. (B) graph of comparison of the results obtained for the two methods (conventional method and continuous method) for the oxygen isotopes.

For this experiment, the default parameters are the following:
pump speed: 40 rpm
loop size: 0.5 ml
gas flow: 80 ml/min
The results are presented in FIGS. 3A and 3B.
The results for each sample tested are detailed in the tables below of FIGS. 3A and 3B.

Figure 4A:
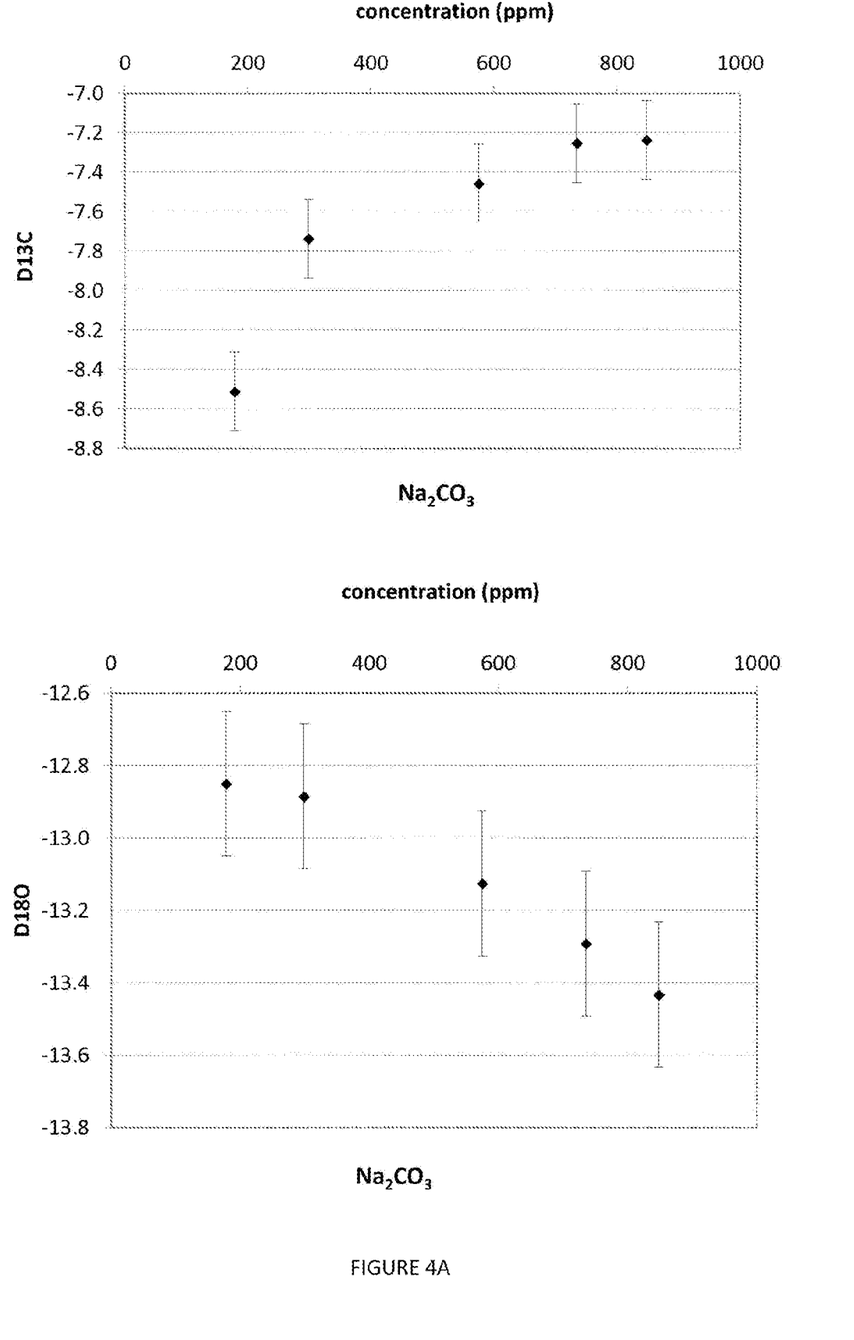
Figure 4B:
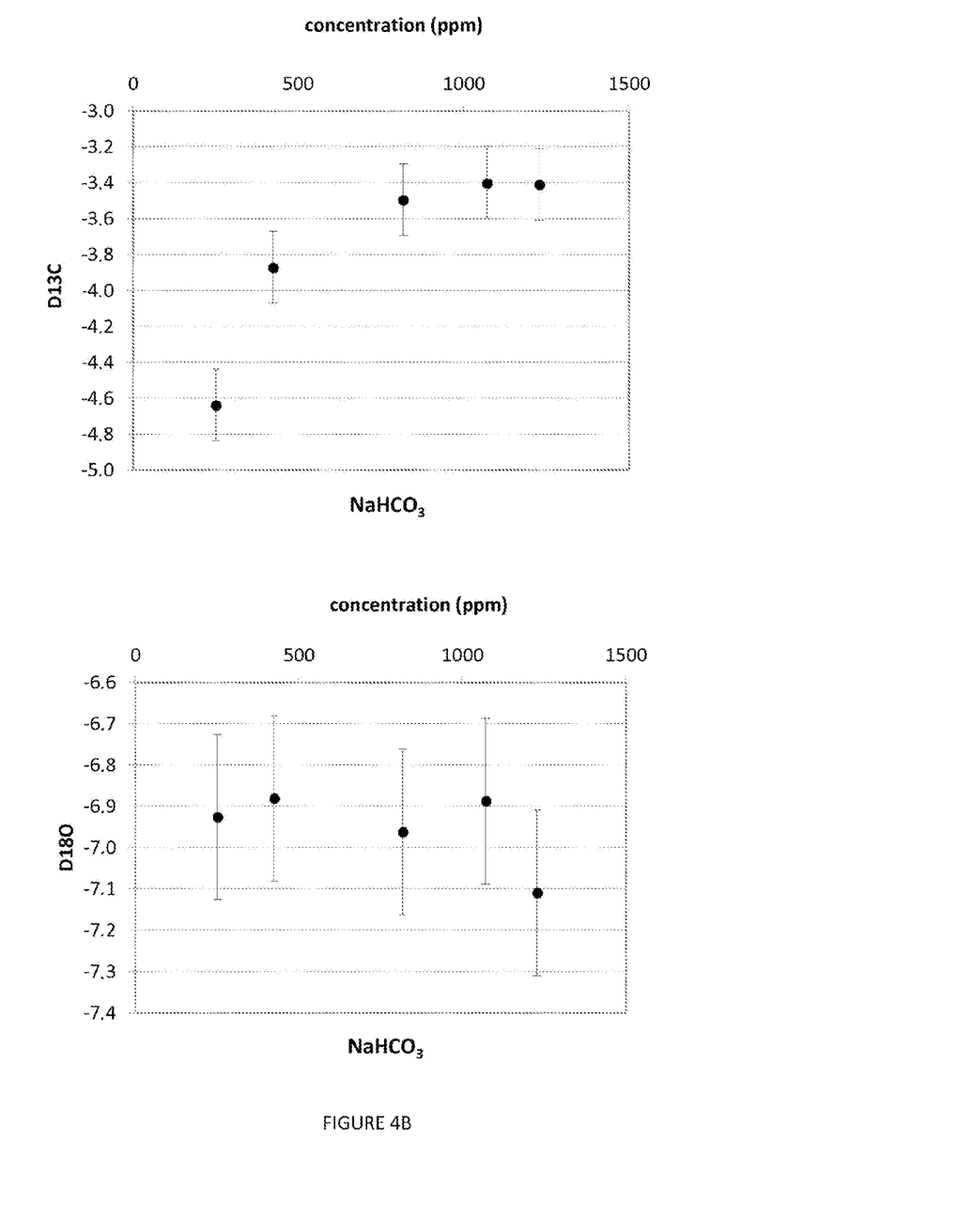

Example 2: Effects of the Concentration on the Isotopic Carbon and Oxygen Values of the Dic of Liquid Samples For this example, two standards (Merck $Na_2CO_3$ for analysis and Merck $NaHCO_3$ for analysis) were prepared. The standards were dissolved in distilled water in order to obtain 5 different concentrations: 150; 300; 600; 800 and 1000 ppm; this made it possible to determine the influence of the $CO_2$ concentration in the solution on the measurement of the $\delta^{13}C$ and of the $\delta^{18}O$ with the hydride generator used according to the present invention. For this experiment, the loop size was fixed at 500 µl and the pump speed at 40 rpm.
The results are presented in FIG. 4.

Example 3: Effects of the Pump Speed on the Concentration and the Isotopic Carbon and Oxygen Values of the Dic of Liquid Samples For this example wherein the hydride generator was used according to the present invention, 5 peristaltic pump speeds were tested: 10; 20; 40; 60 and 80 rpm. For this experiment, the loop size was fixed at 500 µl and 3 samples were measured: a Plancoët mineral water, $Na_2CO_3$ (1000 ppm) and $NaHCO_3$ (1000 ppm). It appears that the more the pump speed increases, the higher the $CO_2$ concentration; the exchange between the acid and the sample appears to be more efficient, on the other hand the $\delta^{13}C$ value measured is relatively stable. The $\delta^{18}O$, for low pump speeds, shows a certain variability, probably due to the low $CO_2$ concentrations produced.

Figure 5A:
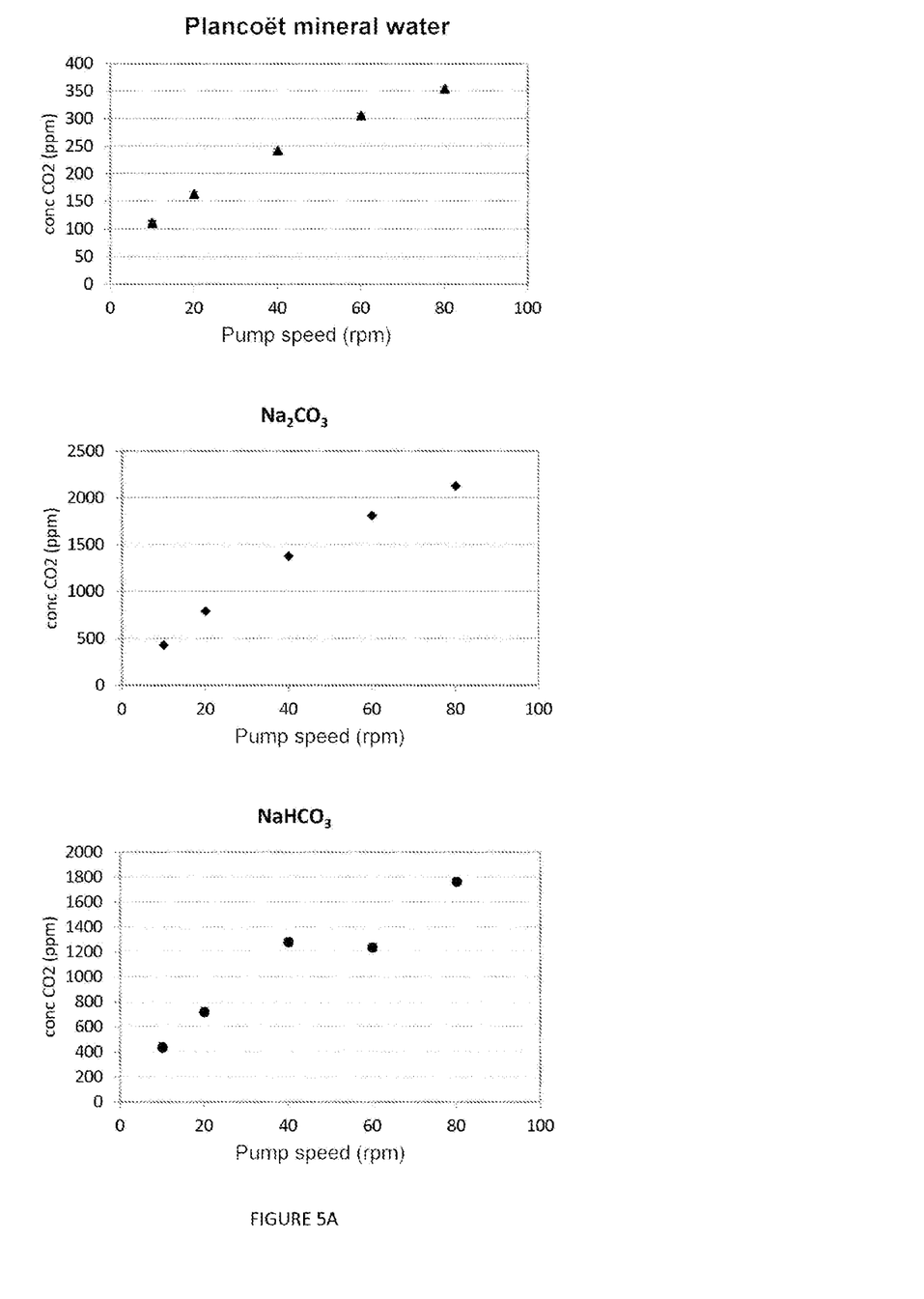
Figure 5B:
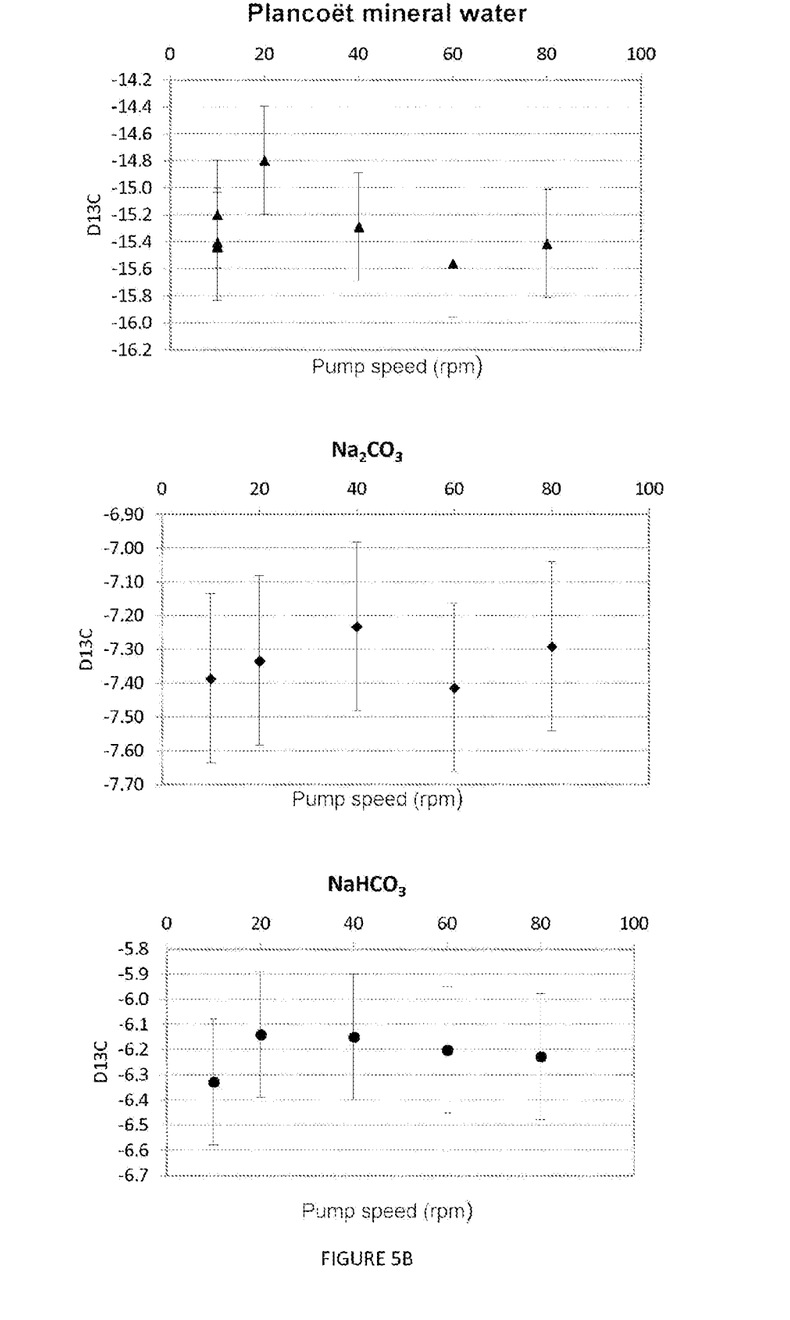
Figure 5C:
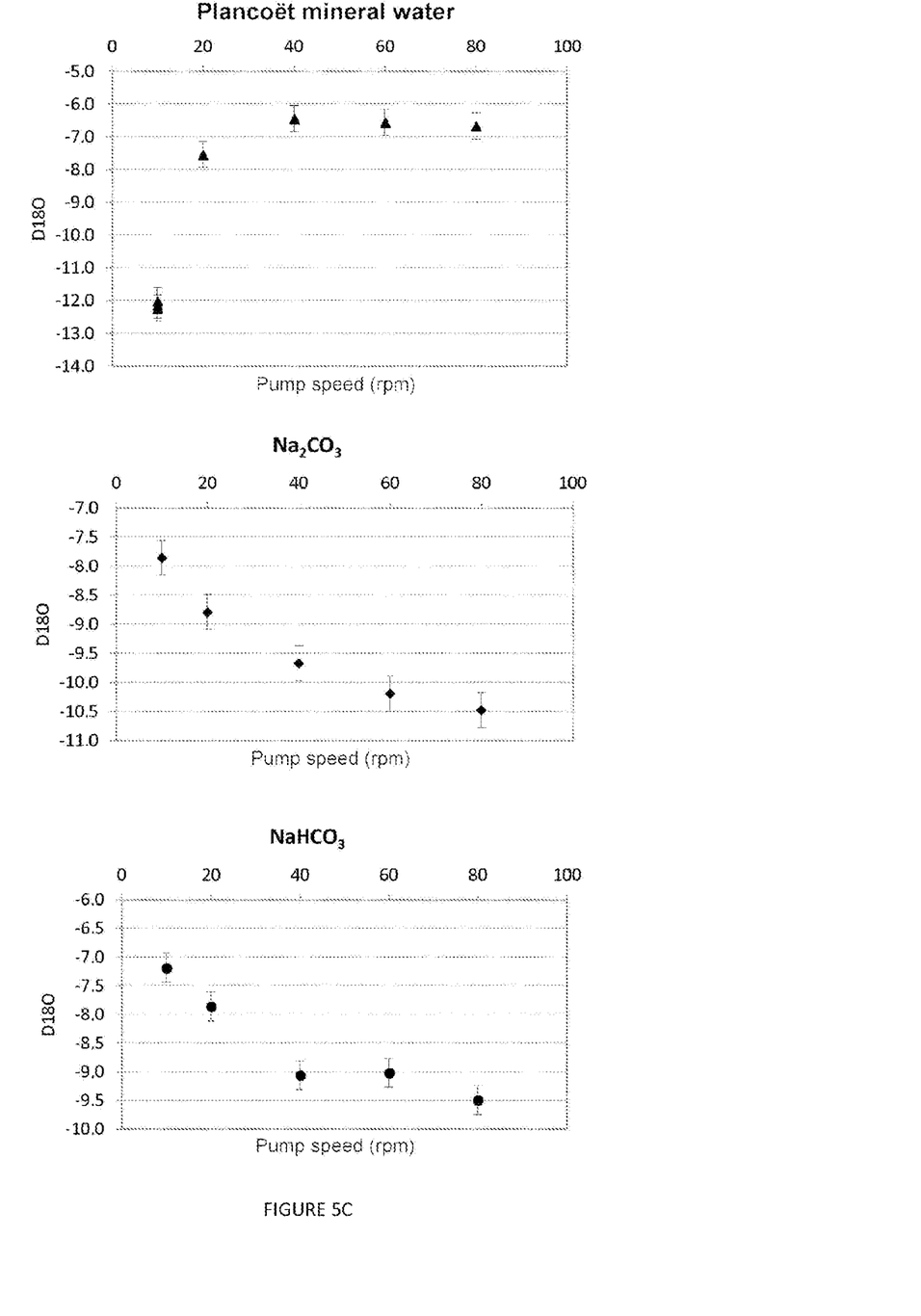

The results are presented in FIG. 5.

Figure 6A:
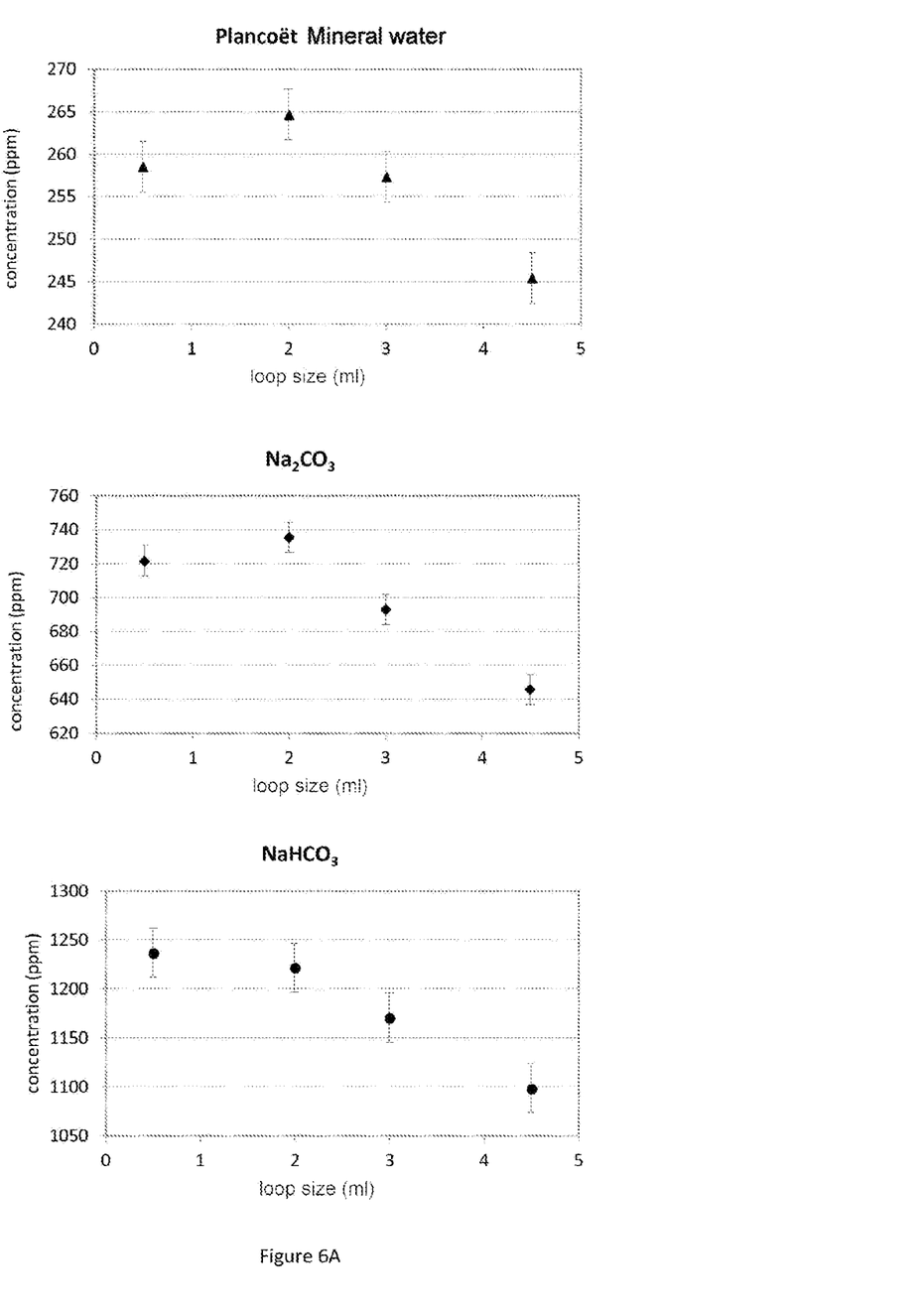
Figure 6B:
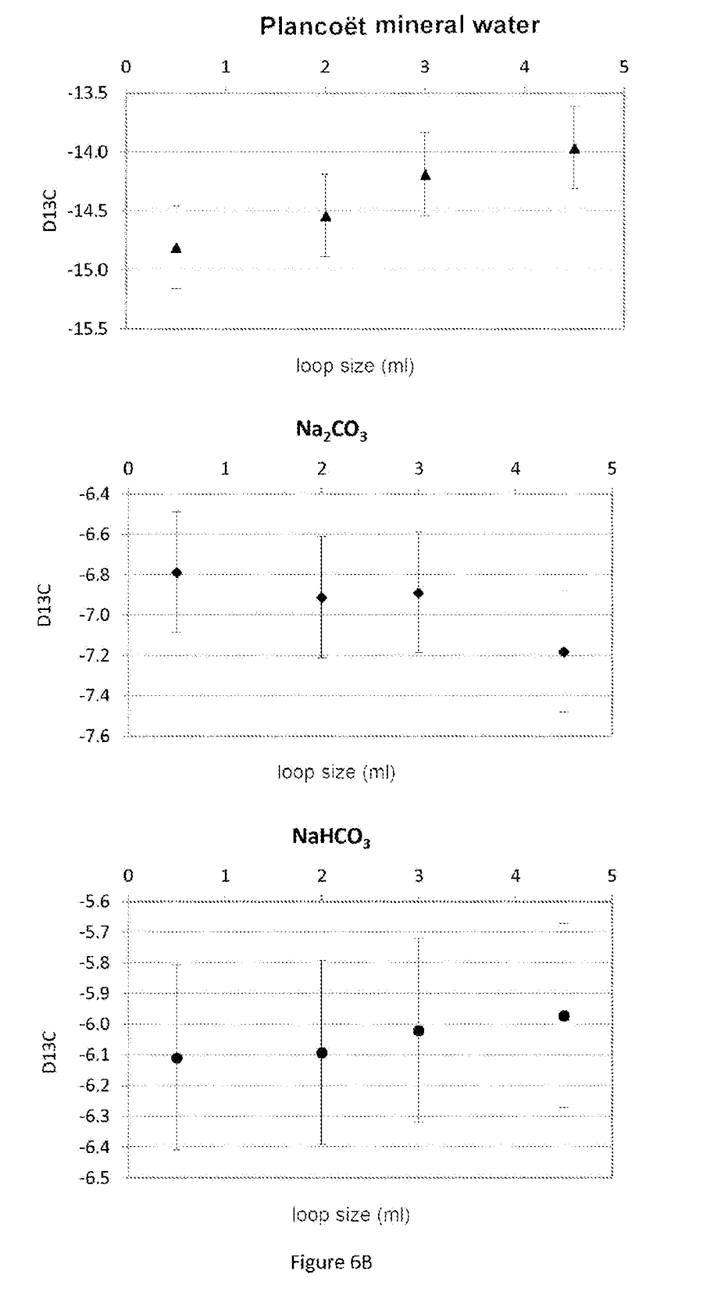
Figure 6C:
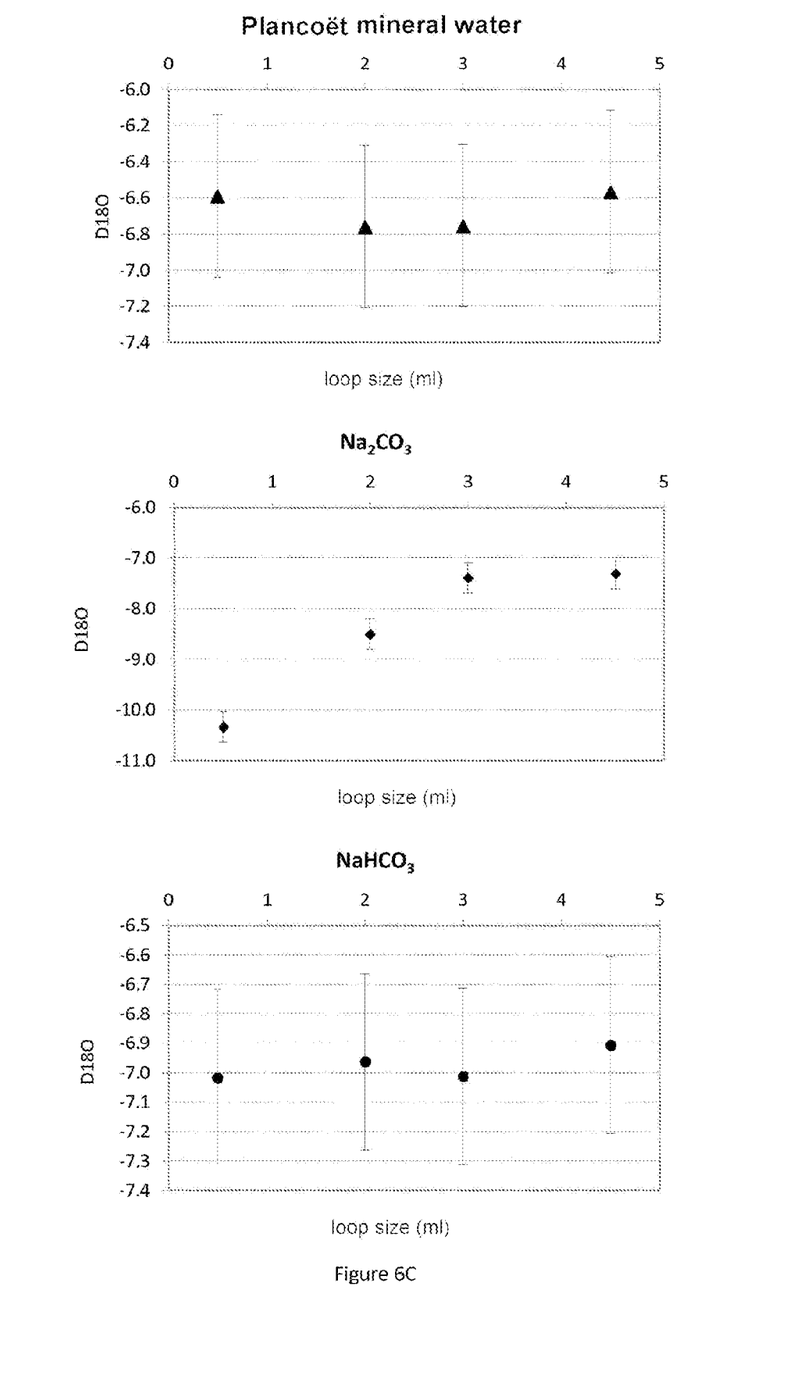
Figure 7:
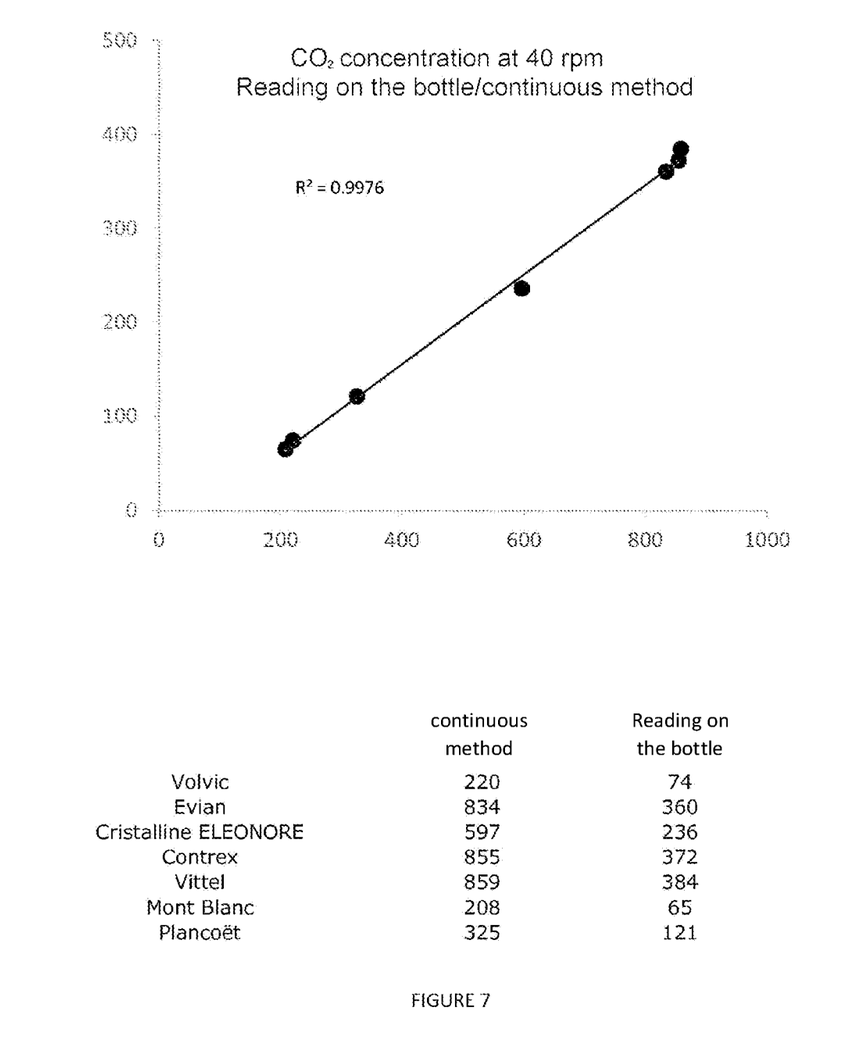
FIG. 7 presents a graph showing a linear relationship between the DIC concentrations read on mineral water bottles and the concentrations deduced from our analyses.

Example 4: Effects of the Length of the Reaction Loop on the $CO_2$ Concentrations and the Isotopic Carbon and Oxygen Values of the Dic of Liquid Samples For this example wherein the hydride generator was used according to the present invention, 4 loop lengths were tested; 0.5; 2; 3 and 4.5 ml. For this experiment, the pump speed was set at 40 rpm and 3 samples were tested: a Plancoët mineral water, $Na_2CO_3$ (1000 ppm) and $NaHCO_3$ (1000 ppm). It appears that the greater the loop size, the more the $CO_2$ concentration decreases; the exchange between the acid and the sample is possibly less efficient.
The results are presented in FIG. 6.

Example 5: Calculation of the Residence Time Under Various Experimental Conditions (Pump Speed, Chamber Volume, Vector-Gas Flow Rate)

For this example, the hydride generator was also used according to the present invention and the characteristics of table (a) below.
(a) Gas-liquid separator configuration used

| | |
|---|---|
| Internal diameter of the tubes for the liquids (mm) | 0.3 |
| Gas flow rate (ml/s) (80 ml/min for Delta Ray) | 1.33 |
| Chamber volume (ml, estimate) | 8 |
| Pump speed (rpm) | 40 |

The results are presented in the tables below.
(b) Calculation of the residence time (RT) of the $CO_2$ by the known continuous method (seconds)
Total RT=total volume/(total volume×seconds$^{-1}$)
Gas RT=total volume/(gas volume×seconds$^{-1}$)
Total volume=liquid volume+gas volume
(c) Calculation of the residence time (RT) for various pump speeds, in typical configuration

| Total RT (s) | Gas RT | Pump speed (rpm) | Liquid flow rate (µl/s) | Vector-gas flow rate (µl/s) | Total flow rate (pl/s) |
|---|---|---|---|---|---|
| 5.98 | 6.00 | 10 | 4.0 | 1333.3 | 1337.3 |
| 5.96 | 6.00 | 20 | 7.9 | 1333.3 | 1341.2 |
| 5.95 | 6.00 | 30 | 11.9 | 1333.3 | 1345.2 |
| 5.93 | 6.00 | 40 | 15.8 | 1333.3 | 1349.1 |
| 5.91 | 6.00 | 50 | 19.8 | 1333.3 | 1353.1 |
| 5.90 | 6.00 | 60 | 23.7 | 1333.3 | 1357.0 |
| 5.88 | 6.00 | 70 | 27.7 | 1333.3 | 1361.0 |

(d) Calculation of the residence time (RT) for various chamber volumes in typical configuration

| Total RT (s) | Gas RT | Chamber volume (ml) | Liquid flow rate (µl/s) | Vector-gas flow rate (µl/s) | Total flow rate (µl/s) |
|---|---|---|---|---|---|
| 0.37 | 0.38 | 0.5 | 15.8 | 1333.3 | 1349.1 |
| 0.74 | 0.75 | 1 | 15.8 | 1333.3 | 1349.1 |
| 1.48 | 1.50 | 2 | 15.8 | 1333.3 | 1349.1 |
| 2.96 | 3.00 | 4 | 15.8 | 1333.3 | 1349.1 |
| 5.93 | 6.00 | 8 | 15.8 | 1333.3 | 1349.1 |
| 11.86 | 12.00 | 16 | 15.8 | 1333.3 | 1349.1 |
| 23.72 | 24.00 | 32 | 15.8 | 1333.3 | 1349.1 |

(e) Calculation of the residence time (RT) for various vector-gas flow rates

| Total RT (s) | Gas RT | Liquid flow rate (µl/s) | Vector-gas flow rate (µl/s) | Total flow rate (µl/s) |
|---|---|---|---|---|
| 69.08 | 80.00 | 15.8 | 100.0 | 115.8 |
| 37.07 | 40.00 | 15.8 | 200.0 | 215.8 |
| 19.24 | 20.00 | 15.8 | 400.0 | 415.8 |
| 9.81 | 10.00 | 15.8 | 800.0 | 815.8 |
| 4.95 | 5.00 | 15.8 | 1600.0 | 1615.8 |
| 2.49 | 2.50 | 15.8 | 3200.0 | 3215.8 |
| 1.25 | 1.25 | 15.8 | 6400.0 | 6415.8 |

The results show that the total average residence time using this type of assembly is calculated at approximately 6 s. It is possible to decrease this time to 1 s by decreasing the volume of the separation chamber.

REFERENCE LIST

1. Method 4500-CO2 in Rice E W, Bridgewater L, Association APH, Association AWW, Federation WE«Standard Methods for the Exalination of Water and Wastewater», Am. Public Health Assn., 2012
2. Assayag et al., Rapid Communications in Mass Spectrometry, 20: 2243-2251, 2006
3. Bass et al., Rapid Communications in Mass Spectrometry, 26: 639-644, 2012
4. Patent application US 2010/0212406
5. Using Isotope Ratio Infrared Spectrometer to determine 513C and δ18O of carbonate samples
6. Smajgl et al. 2017, 19th EGU General Assembly, EGU2017, proceedings from the conference held Apr. 23-28, 2017 in Vienna, Austria., p. 9793

The invention claimed is:

1. A device for continuous analysis of a concentration of dissolved inorganic carbon (DIC) and/or of isotopic carbon and oxygen compositions thereof in a liquid sample, said device comprising:
    a plurality of reservoirs, each comprising a fluid;
    an assembly of tubes, each connected to one of the plurality of reservoirs, each containing a fluid, and connected to a pump positioned downstream of said tubes;
    a mixing chamber positioned downstream of the pump and wherein the fluids conveyed to the pump are dynamically mixed;
    a reaction loop positioned downstream of the mixing chamber, said reaction loop making it possible to convert the DIC into $CO_2$ gas according to an acid-base reaction;
    a separation chamber positioned downstream of the reaction loop, said separation chamber also being connected to a vector-gas cylinder containing $CO_2$-free vector gas;
    a pressure regulator and a control unit positioned between the vector-gas cylinder and the separation chamber and which control a flow of CO2-free vector gas sent from the vector-gas cylinder into the separation chamber for capturing the $CO_2$ gas produced in the reaction loop;
    a waste reservoir positioned downstream of the separation chamber for recovering, via the pump, a residual fluid;
    a water- and particle-trap positioned downstream of the separation chamber;
    optionally, an open-split positioned between the separation chamber and the water- and particle-trap in order to adjust a flow of $CO_2$-loaded vector gas; and
    a detection system positioned downstream of the water- and particle-trap.
2. The device as claimed in claim 1, wherein the separation chamber comprises a wall with an extended and treated surface for optimizing degassing.
3. The device as claimed in claim 2, wherein the wall of the separation chamber is made of frosted glass.
4. The device as claimed in claim 1, wherein the plurality of reservoirs comprise a first reservoir containing the liquid sample and a second reservoir containing an acidifying reagent.
5. The device as claimed in claim 1, wherein the detection system is an analyzer of infrared laser spectrometry type, of cavity ring-down type, or of isotope-ratio infrared spectrometer type.
6. The device as claimed in claim 1, wherein the $CO_2$-free vector gas is chosen from helium and $CO_2$-free synthetic air.
7. A method for continuous analysis of the concentration of dissolved inorganic carbon (DIC) and/or of the isotopic carbon and oxygen compositions thereof in a liquid sample, said method comprising:
    a) conveying the liquid sample to be analyzed and an acidifying reagent to a pump with constant flows F1 and F2, respectively;
    b) injecting and mixing the liquid sample and the acidifying agent in a mixing chamber;
    c) conveying the mixture of fluids obtained in step b) to a reaction loop wherein an acid-base reaction makes it possible to totally or partially convert the DIC into $CO_2$ gas;
    d) conveying a mixture of gas and liquid obtained in step c) into a separation chamber;
    e) injecting a flow of vector gas devoid of $CO_2$ into the separation chamber in order to capture the $CO_2$ gas produced during step c) and released in the separation chamber;
    f) conveying the flow of vector gas containing the $CO_2$, captured in step e), through a water- and particle-trap, optionally after a passage through an open-split for a flow adjustment;
    g) conveying a residual fluid composed of the acidifying reagent and of the degassed sample into a waste reservoir;
    h) conveying the flow of vector gas containing the $CO_2$, captured in step e), into a detection system;
    i) determining the concentration of the DIC and/or the isotopic carbon and oxygen compositions thereof by means of said detection system.
8. The method as claimed in claim 7, wherein step a) is carried out under constant flows F1 of liquid sample and F2 of acidifying reagent of the order of 750 µl/min and 190 µl/min, respectively.
9. The method as claimed in claim 7, wherein step e) is carried out with a reaction loop of which the length ranges from 0.5 to 4.5 ml as a function of the liquid sample to be analyzed.
10. The method as claimed in claim 7, wherein step e) uses a vector gas chosen from helium and $CO_2$-free synthetic air.
11. The method as claimed in claim 7, wherein the flow of $CO_2$-free vector gas is controlled by a pressure regulator and a control unit in order to optimize an amount of $CO_2$ gas arriving at the detection system.

12. The method as claimed in claim 7, wherein step a) is carried out with an acidifying reagent which is an anhydric acid.

13. The method as claimed in claim 7, wherein step i) is carried out by means of an analyzer of isotope-ratio infrared laser spectrometer type.

14. The device as claimed in claim 4, wherein the acidifying agent of the second reservoir is an anhydric acid or an orthophosphoric acid.

15. The method as claimed in claim 12, wherein the acidifying reagent is an orthophosphoric acid.

* * * * *